United States Patent [19]

Hillman et al.

[11] Patent Number: 5,763,589
[45] Date of Patent: Jun. 9, 1998

[54] HUMAN MEMBRANE PROTEIN

[75] Inventors: Jennifer L. Hillman, San Jose; Surya K. Goli, Sunnyvale, both of Calif.

[73] Assignee: Incyte Pharmaceuticals, Inc., Palo Alto, Calif.

[21] Appl. No.: 781,562

[22] Filed: Jan. 9, 1997

[51] Int. Cl.$^6$ .......................... C12N 15/12; C12N 15/63; C07H 21/04
[52] U.S. Cl. .................... 536/23.1; 435/320.1; 536/24.3; 536/24.5
[58] Field of Search ............................. 536/23.1, 24.3, 536/24.5; 435/320.1

[56] References Cited

PUBLICATIONS

Singer, S.J., "The Structure and Insertion of Integral Proteins In Membranes", *Annu. Rev. Cell Biol.* (1990) 6:247–296.

Salzer, U. et al., "Identification of the phosphorylation site on human erythrocyte band 7 integral membrane protein: implications for a monotopic protein structure.", *Biochemica et Biophysica Acta.* (1993) 1151:149–152.

Stewart, G.W. et al., "Stomatin: a putative cation transport regulator in the red cell membrane.", *Biochimica et Biophysica Acta.* (1993) 1225:15–25.

Stewart, G.W. et al., "Isolatio of cDNA Coding for an Ubiquitous Membrane Protein Deficient in High Na+, Low K+ Stomatocytic Erythrocytes", *Blood* (1992) 79(6):1593–1601.

Hiebl–Dirschmied, C.M. et al., "Isolation and partial characterization of the human erythrocyte band 7 integral membrane protein", *Biochimica et Biophysica Acta.* (1991) 1065:195–202.

Desneves, J. et al., "Human Erythrocyte Band 7.2b is Preferentially Labeled Photoreactive Phospholipid", *Biochem.Biophy.Res.Commun.* (1996) 224:108–114.

Snyers, L. et al., "Induction of metallothionein and stomatin by interleukin–6 and glucocorticoids in a human amniotic cell line.", *Eur.J.Biochem.* (1994) 223:411–418.

Huang, M. et al., "A stomatin–like protein necessary for mechanosensation in *C. elegans.*", *Nature* (1995) 378:292–295.

Barnes, T.M. et al., "The *Caenorhabditis elegans* Behavioral Gene *unc*–24 Encodes a Novel Bipartite Protein Similar to Both Erythrocyte Band 7.2 (Stomatin) and Nonspecific Lipid Transfer Protein", *J. Neurochem.* (1996) 67:46–57.

Hiebl–Dirschmied, C.M. et al., "Cloning and nucleotide sequence of cDNA encoding human erythrocyte band 7 integral membrane protein.", *Biochimica et Biophysica Acta.* (1991) 1090:123–124.

Philipp, W.J. et al., "An integrated map of the genome of the tubercle bacillus, Mycobacterium tuberculosis H36Rv, and comparison with Mycobacterium leprae.", *Proc.Natl.Acad.Sci.USA* (1996).

Bult, C.J. et al., "Complete Genome Sequence of the Methanogenic Archaeon, *Methanococcus jannaschii*", *Science* (1996) 273:1058–1073.

Wang, D. et al., "Purification of Band 7.2b, a 31–kDa Integral Phosphoprotein Absent in Hereditary Stomatocytosis", *J. Biol. Chem.* (1991) 266:17826–17831.

Stewart, G.M., "Co–Ordinated Variations in Chloride–Dependent Potassium Transport and Cell Water in Normal Human Erythrocytes", *J. Physio.* (1988) 401:1–16.

Stewart, G.W. et al., "Integral band 7 protein of the humam erythrocyte membrane.", *Biochem.Soc.Trans.* (1992) 20(4):785–790.

Kemp, B.E. et al., "Protein Kinase recognition sequence motifs.", *TIBS* (1990) 15:342–346.

Salzer, U et al (1993) Biochem. Biophys. Acta 1151:149–152.

Huang, M et al (1995) Nature 378:292–295.

Barnes, TM et al (1996) J Neurochem. 67:46–57.

*Primary Examiner*—Toni R. Scheiner
*Assistant Examiner*—Geetha P. Bansal
*Attorney, Agent, or Firm*—Lucy J. Billings

[57] ABSTRACT

The present invention provides a novel human integral membrane (IMP) and polynucleotides which identify and encode IMP. The invention also provides genetically engineered expression vectors and host cells comprising the nucleic acid sequences encoding IMP and a method for producing IMP. The invention also provides for agonists, antibodies, or antagonists specifically binding IMP, and their use, in the prevention and treatment of diseases associated with expression of IMP. Additionally, the invention provides for the use of antisense molecules to polynucleotides encoding IMP for the treatment of diseases associated with the expression of IMP. The invention also provides diagnostic assays which utilize the polynucleotide, or fragments or the complement thereof, and antibodies specifically binding IMP.

8 Claims, 8 Drawing Sheets

```
                                   9              18              27              36              45              54
5' GGC TTC TGG GAG CNA CCG CTC CGC TCG TCT CGT TGG TTC CGG AGG TCG CTG CGG 63              72              81              90              99             108
   CGG TGG GAA ATG CTG GCG CGC GCG CGG GGG CAC TGG GGC CCT TTT GCT GAG
                    M   L   A   R   A   R   G   H   W   G   P   F   A   E 117             126             135             144             153             162
   GGG CTC TCT ACT GGC TTC TGG CCG CGC TCC CGC GCC TCC GGA TTG CCC
    G   L   S   T   G   F   W   P   R   S   R   A   S   G   L   P 171             180             189             198             207             216
   CGA AAC ACC GTG GTA CTG TTC GTG CCG CAG CAG GAG GCC TGG GTG GTG GAG CGA
    R   N   T   V   V   L   F   V   P   Q   Q   E   A   W   V   V   E   R 225             234             243             252             261             270
   ATG GGC CGA TTC CAC CGG ATC CTG GAG CCT GGT TTG AAC ATC CTC ATC CCT GTG
    M   G   R   F   H   R   I   L   E   P   G   L   N   I   L   I   P   V 279             288             297             306             315             324
   TTA GAC CGG ATC CGA TAT GTG CAG AGT CTC AAG GAA ATT GTC ATC AAC GTG CCT
    L   D   R   I   R   Y   V   Q   S   L   K   E   I   V   I   N   V   P 333             342             351             360             369             378
   GAG CAG TCG GCT GTG ACT CTC GAC AAT GTA ACT CTG CAA ATC GAT GGA GTC CTT
    E   Q   S   A   V   T   L   D   N   V   T   L   Q   I   D   G   V   L
```

FIGURE 1A

```
TAC CTG CGC ATC ATG GAC CCT TAC AAG GCA AGC TAC GGT GTG GAG GAC CCT GAG
 Y   L   R   I   M   D   P   Y   K   A   S   Y   G   V   E   D   P   E
387         396         405         414         423         432

TAT GCC GTC ACC CAG CTA GCT CAA ACC ATG AGA TCA GAG CTC GGC AAA CTC
 Y   A   V   T   Q   L   A   Q   T   M   R   S   E   L   G   K   L
441         450         459         468         477         486

TCT NTG GAC AAA GTC TTC CGG GAA TCC GAG TCC AAT GCC CTG AGC ATT GTG GAT
 S   X   D   K   V   F   R   E   S   E   S   N   A   L   S   I   V   D
495         504         513         522         531         540

GCC AAC CAA GCT GAC TGC TGG GGT ATC CGC TGC CTN CGT TAT GAG ATC
 A   N   Q   A   D   C   W   G   I   R   C   L   R   Y   E   I
549         558         567         576         585         594

AAG GAT ATC CAT GTG CCA CCC CGG GTG AAA GAG TCT ATG CAG ATG CAG GTG GAG
 K   D   I   H   V   P   P   R   V   K   E   S   M   Q   M   Q   V   E
603         612         621         630         639         648

GCA GAG CGG AAA CGG GCC ACA GTT CTA GAG GGG TCT GAG ACC CGA GAG TCG
 A   E   R   K   R   A   T   V   L   E   G   S   E   T   R   E   S
657         666         675         684         693         702

GCA AAT GTG GCA GAA GGG AAA AAA CAG GCC CAG ATC CTG GCC TCC GAA GCA
 A   N   V   A   E   G   K   K   Q   A   Q   I   L   A   S   E   A
711         720         729         738         747         756
```

FIGURE 1B

```
      765             774         783         792         801         810
GAA AAG GCT GAA CAG ATA AAT CAG GCA GCA GGA GAG GCC AGT GCA GTT CTG GCG
 E   K   A   E   Q   I   N   Q   A   A   G   E   A   S   A   V   L   A 819             828         837         846         855         864
AAG GCC AAG GCT AAA GCT GAA GCT ATT CGA ATC CTG GCT GCA GCT CTG ACA CAA
 K   A   K   A   K   A   E   A   I   R   I   L   A   A   A   L   T   Q 873             882         891         900         909         918
CAT AAT GGA GAT GCA GCA GCT TCA CTG ACT GTG GCC GAG CAG TAT GTC AGC GCG
 H   N   G   D   A   A   A   S   L   T   V   A   E   Q   Y   V   S   A 927             936         945         954         963         972
TTC TCC AAA CTG GCC AAG GAC TCC AAC ACT ATC CTA CTG CCC TCC AAC CCT GGC
 F   S   K   L   A   K   D   S   N   T   I   L   L   P   S   N   P   G 981             990         999         1008        1017        1026
GAT GTC ACC AGC ATG GTG GCT CAG GCC ATG GGT TAT GGA GCC CTC ACC AAA
 D   V   T   S   M   V   A   Q   A   M   G   Y   G   A   L   T   K 1035            1044        1053        1062        1071        1080
GCC CCA GTG CCA GGG ACT CCA GAC TCA CTC TCC AGT GGG AGC AGC AGA GAT GTC
 A   P   V   P   G   T   P   D   S   L   S   S   G   S   S   R   D   V 1089            1098        1107        1116        1125        1134
CAG GGT ACA GAT GCA AGT NTT GAT GAG GAA CTT GAT CGA GTC AAG ATG AGT TAG
 Q   G   T   D   A   S   X   D   E   E   L   D   R   V   K   M   S   *
```

FIGURE 1C

```
      765            774       783       792       801       810
GAA AAG GCT GAA CAG ATA AAT CAG GCA GCA GGA GAG GCC AGT GCA GTT CTG GCG
 E   K   A   E   Q   I   N   Q   A   A   G   E   A   S   A   V   L   A 819            828       837       846       855       864
AAG GCC AAG GCT AAA GCT GAA GCT ATT CGA GGA CTG GCT GCA GCT CTG ACA CAA
 K   A   K   A   K   A   E   A   I   R   G   L   A   A   L   T   Q 873            882       891       900       909       918
CAT AAT GGA GAT GCA GCA GCT TCA CTG ACT GTG GCC GAG CAG TAT GTC AGC GCG
 H   N   G   D   A   A   A   S   L   T   V   A   E   Q   Y   V   S   A 927            936       945       954       963       972
TTC TCC AAA CTG GCC AAG GAC TCC AAC ACT ATC CTA CTG CCC TCC AAC CCT GGC
 F   S   K   L   A   K   D   S   N   T   I   L   L   P   S   N   P   G 981            990       999      1008      1017      1026
GAT GTC ACC AGC ATG GTG GCT CAG GCC ATG GGT GTA TAT GGA GCC CTC ACC AAA
 D   V   T   S   M   V   A   Q   A   M   G   V   Y   G   A   L   T   K 1035           1044      1053      1062      1071      1080
GCC CCA GTG CCA GGG ACT CCA GAC TCA CTC TCC AGT GGG AGC AGC CTC ACC GTC
 A   P   V   P   G   T   P   D   S   L   S   S   G   S   S   L   T   V 1089           1098      1107      1116      1125      1134
CAG GGT ACA GAT GCA AGT NTT GAT GAG GAA CTT GAT CGA GTC AAG ATG AGT TAG
 Q   G   T   D   A   S   X   D   E   E   L   D   R   V   K   M   S   *
```

```
330 SLSSGSSRDVQG-----------TDASXDEELD---RVK--------  789094
276 S------------------------------------L--------  GI 31069
276 S------------------------------------S--------  GI 1065452
364 VVFFE-TSLEVFGKILTKEVSPVTVYMNGNLKVKGSIQDAM       GI 1353669
333 HAADGDDAEVAGWFSTDTDPSIARAVA--TAEAIARKPV         Z79701

355 ---------MS          789094
277 Q-GIIGAKHSHLG        GI 31069
277 D-GI------S          GI 1065452
403 QLKHLVERMSDWL        GI 1353669
370 E-GSLGTPPPRLTQ       Z79701
```

FIGURE 2C

| Library | Lib Description | Abun | Pct Abun |
|---|---|---|---|
| PROSTUT03 | prostate tumor, 67 M, match to PROSNOT05 | 2 | 0.0703 |
| COLNNOT05 | colon, 40 M, match to COLNCRT01 | 2 | 0.0577 |
| TESTNOT03 | testis, 37 M | 1 | 0.0557 |
| LIVRNOT02 | liver, 32 F | 1 | 0.0515 |
| HUVENOB01 | HUVEC endothelial cell line, control | 1 | 0.0418 |
| LVENNOT03 | heart, left ventricle, 31 M | 1 | 0.0336 |
| PROSTUT01 | prostate tumor, 50 M, match to PROSNOT02 | 1 | 0.0309 |
| PANCTUT02 | pancreatic tumor, carcinoma, 45 F | 1 | 0.0288 |
| KERANOT01 | keratinocytes, neonatal M | 1 | 0.0227 |
| CRBLNOT01 | brain, cerebellum, 69 M | 1 | 0.0194 |
| LUNGNOT04 | lung, 2 M | 1 | 0.0182 |
| PGANNOT01 | paraganglia, 46 M | 1 | 0.0159 |
| BRSTTUT01 | breast tumor, 55 F, match to BRSTNOT02 | 1 | 0.0150 |

FIGURE 3

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 356 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: Consensus
        ( B ) CLONE: Consensus ( x i ) SEQUENCE DESCRIPTION: SEQ ID NO:1:

```
Met Leu Ala Arg Ala Ala Arg Gly His Trp Gly Pro Phe Ala Glu Gly
 1               5                  10                  15
Leu Ser Thr Gly Phe Trp Pro Arg Ser Gly Arg Ala Ser Ser Gly Leu
            20                  25                  30
Pro Arg Asn Thr Val Val Leu Phe Val Pro Gln Gln Glu Ala Trp Val
             35                  40                 45
Val Glu Arg Met Gly Arg Phe His Arg Ile Leu Glu Pro Gly Leu Asn
     50                  55                  60
Ile Leu Ile Pro Val Leu Asp Arg Ile Arg Tyr Val Gln Ser Leu Lys
 65                 70                  75                  80
Glu Ile Val Ile Asn Val Pro Glu Gln Ser Ala Val Thr Leu Asp Asn
                 85                  90                  95
Val Thr Leu Gln Ile Asp Gly Val Leu Tyr Leu Arg Ile Met Asp Pro
            100                 105                 110
Tyr Lys Ala Ser Tyr Gly Val Glu Asp Pro Glu Tyr Ala Val Thr Gln
            115                 120                 125
Leu Ala Gln Thr Thr Met Arg Ser Glu Leu Gly Lys Leu Ser Xaa Asp
    130                 135                 140
Lys Val Phe Arg Glu Arg Glu Ser Leu Asn Ala Ser Ile Val Asp Ala
145                 150                 155                 160
Ile Asn Gln Ala Ala Asp Cys Trp Gly Ile Arg Cys Leu Arg Tyr Glu
                165                 170                 175
Ile Lys Asp Ile His Val Pro Pro Arg Val Lys Glu Ser Met Gln Met
            180                 185                 190
Gln Val Glu Ala Glu Arg Arg Lys Arg Ala Thr Val Leu Glu Ser Glu
            195                 200                 205
Gly Thr Arg Glu Ser Ala Ile Asn Val Ala Glu Gly Lys Lys Gln Ala
    210                 215                 220
```

```
Gln Ile Leu Ala Ser Glu Ala Glu Lys Ala Glu Gln Ile Asn Gln Ala
225                 230                 235                 240

Ala Gly Glu Ala Ser Ala Val Leu Ala Lys Ala Lys Ala Lys Ala Glu
                245                 250                 255

Ala Ile Arg Ile Leu Ala Ala Ala Leu Thr Gln His Asn Gly Asp Ala
            260                 265                 270

Ala Ala Ser Leu Thr Val Ala Glu Gln Tyr Val Ser Ala Phe Ser Lys
        275                 280                 285

Leu Ala Lys Asp Ser Asn Thr Ile Leu Leu Pro Ser Asn Pro Gly Asp
    290                 295                 300

Val Thr Ser Met Val Ala Gln Ala Met Gly Val Tyr Gly Ala Leu Thr
305                 310                 315                 320

Lys Ala Pro Val Pro Gly Thr Pro Asp Ser Leu Ser Ser Gly Ser Ser
                325                 330                 335

Arg Asp Val Gln Gly Thr Asp Ala Ser Xaa Asp Glu Glu Leu Asp Arg
            340                 345                 350

Val Lys Met Ser
            355
```

( 2 ) INFORMATION FOR SEQ ID NO:2:

( i ) SEQUENCE CHARACTERISTICS:
        ( A ) LENGTH: 1188 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: Consensus
        ( B ) CLONE: Consensus ( x i ) SEQUENCE DESCRIPTION: SEQ ID NO:2:

```
GGCTTCTGGG AGCNACCGCT CCGCTCGTCT CGTTGGTTCC GGAGGTCGCT GCGGCGGTGG    60
GAAATGCTGG CGCGCGCGGC GCGGGGGCAC TGGGGCCCTT TGCTGAGGG GCTCTCTACT   120
GGCTTCTGGC CGCGCTCCGG CCGCGCCTCC TCTGGATTGC CCGAAACAC CGTGGTACTG   180
TTCGTGCCGC AGCAGGAGGC CTGGGTGGTG GAGCGAATGG GCCGATTCCA CCGGATCCTG   240
GAGCCTGGTT TGAACATCCT CATCCCTGTG TTAGACCGGA TCCGATATGT GCAGAGTCTC   300
AAGGAAATTG TCATCAACGT GCCTGAGCAG TCGGCTGTGA CTCTCGACAA TGTAACTCTG   360
CAAATCGATG GAGTCCTTTA CCTGCGCATC ATGGACCCTT ACAAGGCAAG CTACGGTGTG   420
GAGGACCCTG AGTATGCCGT CACCCAGCTA GCTCAAACAA CCATGAGATC AGAGCTCGGC   480
AAACTCTCTN TGGACAAAGT CTTCCGGGAA CGGGAGTCCC TGAATGCCAG CATTGTGGAT   540
GCCATCAACC AAGCTGCTGA CTGCTGGGGT ATCCGCTGCC TNCGTTATGA GATCAAGGAT   600
ATCCATGTGC CACCCGGGGT GAAAGAGTCT ATGCAGATGC AGGTGGAGGC AGAGCGGCGG   660
AAACGGGCCA CAGTTCTAGA GTCTGAGGGG ACCCGAGAGT CGGCCATCAA TGTGGCAGAA   720
GGGAAGAAAC AGGCCCAGAT CCTGGCCTCC GAAGCAGAAA AGGCTGAACA GATAAATCAG   780
GCAGCAGGAG AGGCCAGTGC AGTTCTGGCG AAGGCCAAGG CTAAAGCTGA AGCTATTCGA   840
ATCCTGGCTG CAGCTCTGAC ACAACATAAT GGAGATGCAG CAGCTTCACT GACTGTGGCC   900
GAGCAGTATG TCAGCGCGTT CTCCAAACTG GCCAAGGACT CCAACACTAT CCTACTGCCC   960
TCCAACCCTG GCGATGTCAC CAGCATGGTG GCTCAGGCCA TGGGTGTATA TGGAGCCCTC  1020
ACCAAAGCCC CAGTGCCAGG GACTCCAGAC TCACTCTCCA GTGGGAGCAG CAGAGATGTC  1080
CAGGGTACAG ATGCAAGTNT TGATGAGGAA CTTGATCGAG TCAAGATGAG TTAGTGGAGC  1140
```

TGGGCTTNGC CAGGGAGTCT GGGGACAAGG AAGCAGATTT TCCTGATT                1188

( 2 ) INFORMATION FOR SEQ ID NO:3:

( i ) SEQUENCE CHARACTERISTICS:
        ( A ) LENGTH: 288 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: Genbank
        ( B ) CLONE: 31069

( x i ) SEQUENCE DESCRIPTION: SEQ ID NO:3:

```
Met Ala Glu Lys Arg His Thr Arg Asp Ser Glu Ala Gln Arg Leu Pro
 1               5                  10                  15
Asp Ser Phe Lys Asp Ser Pro Ser Lys Gly Leu Gly Pro Cys Gly Trp
                20                  25                  30
Ile Leu Val Ala Phe Ser Phe Leu Phe Thr Val Ile Thr Phe Pro Ile
                35                  40                  45
Ser Ile Trp Met Cys Ile Lys Ile Ile Lys Glu Tyr Glu Arg Ala Ile
 50                  55                  60
Ile Phe Arg Leu Gly Arg Ile Leu Gln Gly Gly Ala Lys Gly Pro Gly
 65                  70                  75                  80
Leu Phe Phe Ile Leu Pro Cys Thr Asp Ser Phe Ile Lys Val Asp Met
                85                  90                  95
Arg Thr Ile Ser Phe Asp Ile Pro Pro Gln Glu Ile Leu Thr Lys Asp
                100                 105                 110
Ser Val Thr Ile Ser Val Asp Gly Val Val Tyr Tyr Arg Val Gln Asn
                115                 120                 125
Ala Thr Leu Ala Val Ala Asn Ile Thr Asn Ala Asp Ser Ala Thr Arg
    130                 135                 140
Leu Leu Ala Gln Thr Thr Leu Arg Asn Val Leu Gly Thr Lys Asn Leu
145                 150                 155                 160
Ser Gln Ile Leu Ser Asp Arg Glu Glu Ile Ala His Asn Met Gln Ser
                165                 170                 175
Thr Leu Asp Asp Ala Thr Asp Ala Trp Gly Ile Lys Val Glu Arg Val
                180                 185                 190
Glu Ile Lys Asp Val Lys Leu Pro Val Gln Leu Gln Arg Ala Met Ala
                195                 200                 205
Ala Glu Ala Glu Ala Ser Arg Glu Ala Arg Ala Lys Val Ile Ala Ala
    210                 215                 220
Glu Gly Glu Met Asn Ala Ser Arg Ala Leu Lys Glu Ala Ser Met Val
225                 230                 235                 240
Ile Thr Glu Ser Pro Ala Ala Leu Gln Leu Arg Tyr Leu Gln Thr Leu
                245                 250                 255
Thr Thr Ile Ala Ala Glu Lys Asn Ser Thr Ile Val Phe Pro Leu Pro
                260                 265                 270
Ile Asp Met Leu Gln Gly Ile Ile Gly Ala Lys His Ser His Leu Gly
                275                 280                 285
```

( 2 ) INFORMATION FOR SEQ ID NO:4:

( i ) SEQUENCE CHARACTERISTICS:
        ( A ) LENGTH: 280 amino acids
        ( B ) TYPE: amino acid
        ( C ) STRANDEDNESS: single
        ( D ) TOPOLOGY: linear (vii) IMMEDIATE SOURCE:
    (A) LIBRARY: GenBank
    (B) CLONE: 1065452

(xi) SEQUENCE DESCRIPTION: SEQ ID NO:4:

```
Met Asn Leu Lys Thr Cys Ser Leu Ser Thr His Ser Phe Leu Gln Lys
 1               5                  10                  15
Lys Asn Glu Lys His Asp Gly Asn Pro Glu His Tyr Asp Thr Gly Leu
            20                  25                  30
Gly Phe Cys Gly Trp Phe Leu Met Gly Leu Ser Trp Ile Met Val Ile
        35                  40                  45
Ser Thr Phe Pro Val Ser Ile Tyr Phe Cys Met Lys Val Val Gln Glu
    50                  55                  60
Tyr Glu Arg Ala Val Ile Phe Arg Leu Gly Arg Leu Ile Gly Gly Gly
65                  70                  75                  80
Ala Lys Gly Pro Gly Ile Phe Phe Val Leu Pro Cys Ile Glu Ser Tyr
                85                  90                  95
Thr Lys Val Asp Leu Arg Thr Val Phe Ser Val Pro Pro Gln Glu
            100                 105                 110
Ile Leu Thr Lys Asp Ser Val Thr Thr Ser Val Asp Ala Val Ile Tyr
        115                 120                 125
Tyr Arg Ile Ser Asn Ala Thr Val Ser Val Ala Asn Val Glu Asn Ala
    130                 135                 140
His His Ser Thr Arg Leu Leu Ala Gln Thr Thr Leu Arg Asn Met Leu
145                 150                 155                 160
Gly Thr Arg Ser Leu Ser Glu Ile Leu Ser Asp Arg Glu Thr Leu Ala
                165                 170                 175
Ala Ser Met Gln Thr Ile Leu Asp Glu Ala Thr Glu Ser Trp Gly Ile
            180                 185                 190
Lys Val Glu Arg Val Glu Ile Lys Asp Val Arg Leu Pro Ile Gln Leu
        195                 200                 205
Gln Arg Ala Met Ala Ala Glu Ala Glu Ala Thr Arg Glu Ala Arg Ala
    210                 215                 220
Lys Val Ile Ala Ala Glu Gly Glu Gln Lys Ala Ser Arg Ala Leu Arg
225                 230                 235                 240
Asp Ala Ala Ser Val Ile Ala Gln Ser Pro Ala Ala Leu Gln Leu Arg
                245                 250                 255
Tyr Leu Gln Thr Leu Asn Ser Val Ala Arg Glu Lys Phe Asp Asp His
            260                 265                 270
Leu Pro Thr Ser Asp Gly Ile Ser
        275                 280
```

(2) INFORMATION FOR SEQ ID NO:5:

(i) SEQUENCE CHARACTERISTICS:
        (A) LENGTH: 415 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1353669

(xi) SEQUENCE DESCRIPTION: SEQ ID NO:5:

```
Met Glu Tyr Gly Met Pro Glu Gly Ser Tyr Asp Ser Val Phe Thr Tyr
 1               5                  10                  15
Ala Pro Tyr Asn Asp Leu Asp Lys Met Gly Tyr Met Gly Pro Ala Arg
            20                  25                  30
```

Gln Gly Met Met Leu Gly Asn Lys Tyr Gly Asn Phe Thr Tyr Thr Arg
        35                      40                  45

Asp Tyr Gly Val Asn Met Glu Asp Asp Ile Lys Pro Leu Ser Ala Ile
        50                      55                  60

Glu Leu Leu Ile Phe Cys Val Ser Phe Leu Val Val Met Thr Met
65                      70                  75                  80

Pro Leu Ser Leu Leu Phe Ala Leu Lys Phe Ile Ser Thr Ser Glu Lys
                    85                  90                  95

Leu Val Val Leu Arg Leu Gly Arg Ala Gln Lys Thr Arg Gly Pro Gly
                100                 105                 110

Ile Thr Leu Val Ile Pro Cys Ile Asp Thr Thr His Lys Val Thr Met
            115                 120                 125

Ser Ile Thr Ala Phe Asn Val Pro Pro Leu Gln Ile Ile Thr Thr Asp
        130                     135                 140

Arg Gly Leu Val Glu Leu Gly Ala Thr Val Phe Leu Lys Ile Arg Asp
145                     150                 155                 160

Pro Ile Ala Ala Val Cys Gly Val Gln Asp Arg Asn Ala Ser Val Arg
                165                 170                 175

Thr Leu Ala Asn Thr Met Leu Tyr Arg Tyr Ile Ser Lys Lys Arg Ile
                180                 185                 190

Cys Asp Val Thr Ser Ser Gln Asp Arg Arg Ile Ile Ser Ala Asn Leu
            195                 200                 205

Lys Asp Glu Leu Gly Ser Phe Thr Cys Gln Phe Gly Val Glu Ile Thr
        210                     215                 220

Asp Val Glu Ile Ser Asp Val Lys Ile Val Lys Glu Gly Glu Asn Met
225                     230                 235                 240

Gly Met Ser Ala Leu Ser Ser Val Ala Lys Ser Asp Ala Gly Gln Gln
                245                 250                 255

Leu Trp Gln Val Ile Gly Pro Val Phe Glu Asp Phe Ala Lys Glu Cys
            260                 265                 270

Ala Ala Glu Glu Lys Ala Lys Glu Asn Ala Pro Leu Val Asp Leu Ser
        275                     280                 285

Asp Val Pro Ser Thr Ser Ala Gly Thr Ser Thr Asp Thr Pro Asn
        290                     295                 300

Ile Pro Ser Ile Asp Ile Asp His Leu Ile Ser Val Ala Ser Leu Ala
305                     310                 315                 320

Met Asp Glu His Leu Val Arg Leu Ile Gly Arg Val Phe Gln Ile Asn
                325                 330                 335

Cys Lys Asp Ile Glu Pro Ile Cys Ile Asp Leu Lys His Gly Ser Gly
            340                 345                 350

Ser Ala Tyr Lys Gly Thr Ser Leu Asn Pro Asp Val Val Phe Glu Thr
        355                     360                 365

Ser Leu Glu Val Phe Gly Lys Ile Leu Thr Lys Glu Val Ser Pro Val
    370                     375                 380

Thr Val Tyr Met Asn Gly Asn Leu Lys Val Lys Gly Ser Ile Gln Asp
385                     390                 395                 400

Ala Met Gln Leu Lys His Leu Val Glu Arg Met Ser Asp Trp Leu
                405                 410                 415

( 2 ) INFORMATION FOR SEQ ID NO:6:

( i ) SEQUENCE CHARACTERISTICS:
        ( A ) LENGTH: 381 amino acids
        ( B ) TYPE: amino acid
        ( C ) STRANDEDNESS: single (D) TOPOLOGY: linear (vii) IMMEDIATE SOURCE:
    (A) LIBRARY: Owl
    (B) CLONE: 79701

(xi) SEQUENCE DESCRIPTION: SEQ ID NO:6:

```
Met Gln Gly Ala Val Ala Gly Leu Val Phe Leu Ala Val Leu Val Ile
 1               5                  10                  15
Phe Ala Ile Ile Val Val Ala Lys Ser Val Ala Leu Ile Pro Gln Ala
            20                  25                  30
Glu Ala Ala Val Ile Glu Arg Leu Gly Arg Tyr Ser Arg Thr Val Ser
        35                  40                  45
Gly Gln Leu Thr Leu Leu Val Pro Phe Ile Asp Arg Val Arg Ala Arg
    50                  55                  60
Val Asp Leu Arg Glu Arg Val Val Ser Phe Pro Gln Pro Val Ile
65                  70                  75                  80
Thr Glu Asp Asn Leu Thr Leu Asn Ile Asp Thr Val Val Tyr Phe Gln
                85                  90                  95
Val Thr Val Pro Gln Ala Ala Val Tyr Glu Ile Ser Asn Tyr Ile Val
            100                 105                 110
Gly Val Glu Gln Leu Thr Thr Thr Leu Arg Asn Val Val Gly Gly
        115                 120                 125
Met Thr Leu Glu Gln Thr Leu Thr Ser Arg Asp Gln Ile Asn Ala Gln
    130                 135                 140
Leu Arg Gly Val Leu Asp Glu Ala Thr Gly Arg Trp Gly Leu Arg Val
145                 150                 155                 160
Ala Arg Val Glu Leu Arg Ser Ile Asp Pro Pro Ser Ile Gln Ala
                165                 170                 175
Ser Met Glu Lys Gln Met Lys Ala Asp Arg Glu Lys Arg Ala Met Ile
            180                 185                 190
Leu Thr Ala Glu Gly Thr Arg Glu Ala Ala Ile Lys Gln Ala Glu Gly
        195                 200                 205
Gln Lys Gln Ala Gln Ile Leu Ala Ala Glu Gly Ala Lys Gln Ala Ala
    210                 215                 220
Ile Leu Ala Ala Glu Ala Asp Arg Gln Ser Arg Met Leu Arg Ala Gln
225                 230                 235                 240
Gly Glu Arg Ala Ala Ala Tyr Leu Gln Ala Gln Gly Gln Ala Lys Ala
                245                 250                 255
Ile Glu Lys Thr Phe Ala Ala Ile Lys Ala Gly Arg Pro Thr Pro Glu
            260                 265                 270
Met Leu Ala Tyr Gln Tyr Leu Gln Thr Leu Pro Glu Met Ala Arg Gly
        275                 280                 285
Asp Ala Asn Lys Val Trp Val Val Pro Ser Asp Phe Asn Ala Ala Leu
    290                 295                 300
Gln Gly Phe Thr Arg Leu Leu Gly Lys Pro Gly Glu Asp Gly Val Phe
305                 310                 315                 320
Arg Phe Glu Pro Ser Pro Val Glu Asp Gln Pro Lys His Ala Ala Asp
                325                 330                 335
Gly Asp Asp Ala Glu Val Ala Gly Trp Phe Ser Thr Asp Thr Asp Pro
            340                 345                 350
Ser Ile Ala Arg Ala Val Ala Thr Ala Glu Ala Ile Ala Arg Lys Pro
        355                 360                 365
Val Glu Gly Ser Leu Gly Thr Pro Pro Arg Leu Thr Gln
    370                 375                 380
```

( 2 ) INFORMATION FOR SEQ ID NO:7:

( i ) SEQUENCE CHARACTERISTICS:
        ( A ) LENGTH: 199 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 1591514

( x i ) SEQUENCE DESCRIPTION: SEQ ID NO:7:

```
Met Lys Val Asn Asp Met Phe Trp Phe Trp Leu Ile Leu Gly Ile Ile
 1               5                  10                  15
Ala Leu Phe Ile Ile Val Lys Ala Ile Val Ile Val Asn Gln Tyr Glu
            20                  25                  30
Gly Gly Leu Ile Phe Arg Leu Gly Arg Val Ile Gly Lys Leu Lys Pro
        35                  40              45
Gly Ile Asn Ile Ile Ile Pro Phe Leu Asp Val Pro Val Lys Val Asp
    50                      55              60
Met Arg Thr Arg Val Thr Asp Ile Pro Pro Gln Glu Met Ile Thr Lys
65                  70              75                      80
Asp Asn Ala Val Val Lys Val Asp Ala Val Val Tyr Tyr Arg Val Ile
                85                  90                  95
Asp Val Glu Lys Ala Ile Leu Glu Val Glu Asp Tyr Glu Tyr Ala Ile
            100                 105             110
Ile Asn Leu Ala Gln Thr Thr Leu Arg Ala Ile Ile Gly Ser Met Glu
        115                 120                 125
Leu Asp Glu Val Leu Asn Lys Arg Glu Tyr Ile Asn Ser Lys Leu Leu
    130                 135                 140
Glu Ile Leu Asp Arg Glu Thr Asp Ala Trp Gly Val Arg Ile Glu Lys
145                 150             155                 160
Val Glu Val Lys Glu Ile Asp Pro Pro Glu Asp Ile Lys Asn Ala Met
                165                 170                 175
Ala Gln Gln Met Lys Ala Glu Arg Leu Lys Arg Ala Ala Ile Leu Glu
            180                 185                 190
Ala Glu Gly Glu Lys Pro Glu
            195
```

HUMAN MEMBRANE PROTEIN

FIELD OF THE INVENTION

This invention relates to nucleic acid and amino acid sequences of a novel integral membrane protein, IMP, and to the use of these sequences in the diagnosis, prevention, and treatment of disease.

BACKGROUND OF THE INVENTION

Membrane proteins are divided into two groups based upon the ease with which the proteins can be removed from the membrane. Extrinsic or peripheral membrane proteins can be removed using extremes of ionic strength or pH, the use of urea or other disruptors of protein interactions. Intrinsic or integral membrane proteins are released only when the lipid bilayer of the membrane is dissolved by detergent. Extrinsic membrane proteins comprise the constituents of the cytoskeleton such as spectrin and actin. Many cytoskeletal proteins are bound directly to integral membrane proteins or are bound indirectly via other proteins such as ankyrin. Cytoskeletal proteins control the shape and dynamics of the cell membrane through their interactions with motor proteins such as myosin and dynein.

The majority of known integral membrane proteins are transmembrane proteins which have an extracellular, a transmembrane, and an intracellular domain. Transmembrane proteins are typically embedded into the cell membrane by one or more regions comprising 15 to 25 hydrophobic amino acids which are predicted to adopt an α-helical conformation. Transmembrane proteins are classified as bitopic (or Types I and II) and polytopic (or Types III and IV) [Singer, S. J. (1990) Annu. Rev. Cell Biol. 6:247–96]. Bitopic proteins span the membrane once while polytopic proteins contain multiple membrane-spanning segments. A small number of integral membrane proteins, termed monotopic proteins, are partially embedded in the membrane (i.e., they do not span the lipid bilayer). Monotopic proteins may be inserted into the bilayer by a hydrophobic hairpin loop or may be attached to the membrane via bound lipid.

A well characterized monotopic protein is the erythrocyte band 7.2 b protein also termed stomatin [Salzer, U. et al. (1993) Biochem. Biophys. Acta 1151:149–52]. Stomatin is absent in the erythrocytes of patients with hereditary stomatocytosis, an autosomal dominant hemolytic anemia. Hereditary stomatocytosis is characterized by abnormal membrane permeability to univalent cations (e.g., $Na^+$ and $K^+$) which leads to swelling and lysis of erythrocytes [Stewart, G. W. et al. (1993) Biochim. Biophys. Acta 1225:15–25]. It has been proposed that stomatin regulates an ion channel by acting as a plug which blocks a channel which is usually latent or tight in normal cells. Proteins which cross-react with anti-stomatin antibodies and mRNA which cross-hybridizes with stomatin gene sequences are found in a wide variety of human cell types and tissues suggesting that stomatin is a widely distributed regulator of transmembrane cation fluxes (i e., stomatin's functions are not limited to erythroid functions) [Stewart, G. W. et al. (1992) Blood 79:1593–1601 and Hiebl-Dirschmied, C. M. et al. (1991) Biochim. Biophys. Acta 1065:192–202]. In addition to its role in ion transport, it has been proposed that stomatin acts to maintain an asymmetric distribution of phospholipids in erythrocytes and other cell types [Desneves, J (1996) Biochem. Biophys. Res. Comm. 224:108–14]. The expression of stomatin has been shown to be up-regulated by dexamethasone and interleukin 6 in a human amniotic cell line suggesting a role for stomatin in protection of cells from oxidative stress [Snyers, L. and Content, J. (1994) Eur. J. Biochem. 223:411–18].

Stomatin has been shown to bind to the erythrocyte cytoskeleton via its carboxyl region [Stewart G. W. et al. (1992), supra], and thus stomatin may play a role in the regulation of ion channels by providing a link between cytoskeletal proteins and ion channels. Interestingly, stomatin shares structural similarity to the central portion of the Caenorhabditis elegans (C. elegans) MEC-2 protein, a protein necessary for mechanosensation [Huang, M. et al. (1995) Nature 378:292–5]. MEC-2 has been shown to link the mechanosensory channel and microtubule cytoskeleton of the touch receptor neurons. It has been proposed that this linkage permits the opening of the mechanosensory channel via microtubule displacement. Stomatin has been shown to share homology with a domain in another C. elegans protein, the UNC-24 protein. UNC-24 is required for normal locomotion in C. elegans [Barnes, T. M. et al. (1996) J. Neurochem. 67:46–57] and it has been proposed that UNC-24 modulates directly or indirectly an ion channel.

The regulation of ion transport is an extremely important physiologic function as ion transport is involved in a wide variety of cell functions including electrical excitability (i.e., action potential propagation), signaling, sensory transduction, control of $Ca^{2+}$ permeability via voltage-dependent $Ca^{2+}$ channels, and in the control of the volume of intracellular and extracellular compartments. Inherited disorders of ion transport include hereditary stomatocytosis, cystic fibrosis, and a variety of hemolytic anemias (e.g., hydrocytosis and xerocytosis).

The discovery of molecules related to stomatin satisfies a need in the art by providing new diagnostic or therapeutic compositions useful in the treatment of disorders associated with abnormal ion transport or membrane conductance.

SUMMARY OF THE INVENTION

The present invention features a novel integral membrane protein hereinafter designated IMP and characterized as having similarity to human stomatin, the Caenorhabditis elegans proteins MEC-2 and UNC-24, a Mycobacterium tuberculosis protein, and a membrane protein from Methanococcus jannaschii.

Accordingly, the invention features a substantially purified polypeptide having the amino acid sequence shown in SEQ ID NO: 1 or fragments thereof. Preferred fragments of SEQ ID NO: 1 are fragments of about 15 amino acids or greater in length which define fragments unique (i.e., having less than about 25% identity to fragments of another protein) to SEQ ID NO: 1 or which retain biological activity (e.g., regulation of ion channel activity) or immunological activity (i.e., capable of eliciting anti-IMP antibodies).

The present invention further provides isolated and substantially purified polynucleotide sequences encoding the polypeptide comprising the amino acid sequence of SEQ ID NO: 1 or fragments thereof. In a particular aspect, the polynucleotide is the nucleotide sequence of SEQ ID NO: 2 or variants thereof. In another embodiment, the present invention provides polynucleotides comprising fragments of SEQ ID NO: 2 having a length greater than 30 nucleotides. The invention further contemplates fragments of this polynucleotide sequence (i.e., SEQ ID NO: 2) that are at least 50 nucleotides, at least 100 nucleotides, at least 250 nucleotides, and at least 500 nucleotides in length.

In addition, the invention provides polynucleotide sequences which hybridize under stringent conditions to the polynucleotide sequence of SEQ ID NO: 2. In another embodiment the present invention provides a composition comprising an isolated and purified polynucleotide sequence encoding IMP.

The invention provides polynucleotide sequences comprising the complement of SEQ ID NO: 2 or variants thereof; these complementary nucleic acid sequences may comprise the complement of the entire nucleic acid sequence of SEQ ID NO: 2 or fragments thereof. In another embodiment the present invention provides a composition comprising an isolated and purified polynucleotide sequence comprising the complement of SEQ ID NO: 2 or variants thereof.

The invention additionally features nucleic acid sequences encoding polypeptides, oligonucleotides, peptide nucleic acids (PNA), fragments, portions or antisense molecules thereof, and expression vectors and host cells comprising polynucleotides that encode IMP.

In another embodiment, the present invention provides an isolated polynucleotide comprising at least a portion of the nucleic acid sequence of SEQ ID NO: 2 or variants thereof contained on a recombinant expression vector. In yet another embodiment, the expression vector containing the polynucleotide sequence is contained within a host cell. The invention is not limited by the nature of the host cell employed. For example, the host cell may be an E. coli cell, a yeast cell, an insect cell, a mammalian cell, etc.

The present invention also provides a method for producing a polypeptide comprising the amino acid sequence of SEQ ID NO: 1 or fragments thereof, the method comprising the steps of: a) culturing the host cell containing an expression vector containing an isolated polynucleotide encoding at least a fragment of the IMP polypeptide under conditions suitable for the expression of the polypeptide; and b) recovering the polypeptide from the host cell culture.

In another embodiment, the invention provides a pharmaceutical composition comprising a substantially purified human IMP protein having an amino acid sequence of SEQ ID NO: 1 in conjunction with a suitable pharmaceutical carrier.

The invention also provides a purified antibody which binds specifically to a polypeptide comprising at least a portion of the amino acid sequence of SEQ ID NO: 1.

Still further, the invention provides a purified agonist which specifically binds to and modulates the activity of a polypeptide comprising at least a portion of the amino acid sequence of SEQ ID NO: 1. The present invention further provides a pharmaceutical composition comprising a purified agonist which specifically binds to and modulates the activity of a polypeptide comprising at least a portion of the amino acid sequence of SEQ ID NO: 1. In another embodiment, the invention provides a purified antagonist which specifically binds to and modulates the activity of a polypeptide comprising at least a portion of the amino acid sequence of SEQ ID NO: 1. The present invention further provides a pharmaceutical composition comprising a purified antagonist which specifically binds to and modulates the activity of a polypeptide comprising at least a portion of the amino acid sequence of SEQ ID NO: 1.

The invention also provides a method for treating prostate cancer comprising administering to a subject in need of such treatment an effective amount of a pharmaceutical composition comprising a purified antagonist which specifically binds to and modulates the activity of a polypeptide comprising at least a portion of the amino acid sequence of SEQ ID NO: 1.

The invention also provides a method for detection of polynucleotides encoding human IMP in a biological sample comprising the steps of: a) hybridizing a polynucleotide sequence encoding human IMP (SEQ ID NO: 1) to nucleic acid material of a biological sample, thereby forming a hybridization complex; and b) detecting the hybridization complex, wherein the presence of the complex correlates with the presence of a polynucleotide encoding human IMP in the biological sample. In a preferred embodiment, prior to hybridization, the nucleic acid material of the biological sample is amplified by the polymerase chain reaction.

BRIEF DESCRIPTION OF THE FIGURES

FIGS. 1A, 1B, 1C and 1D shows the amino acid sequence (SEQ ID NO: 1) and nucleic acid sequence (SEQ ID NO: 2) of IMP. The alignment was produced using MacDNASIS PRO™ software (Hitachi Software Engineering Co., Ltd., San Bruno, Calif.).

FIGS. 2A, 2B and 2C shows the amino acid sequence alignments among IMP (SEQ ID NO: 1), human erythrocyte band 7 protein (i.e., stomatin) [GI 31069 (SEQ ID NO: 3); Hiebl-Dirschmied, C. M. et al. (1991) Biochem. Biophys. Acta 1090:123-24], C. elegans MEC-2 protein [GI 1065452 (SEQ ID NO: 4); Huang, M. (1995), supra], C elegans UNC-24 protein [GI 1353669 (SEQ ID NO: 5); Barnes, T. M. (1996), supra], a Mycobacterium tuberculosis protein of unknown function [Z79701 (SEQ ID NO: 6)] and a membrane protein from Methanococcus jannaschii [GI 1591514 (SEQ ID NO: 7); Bult, C. J. et al. (1996) Science 273:1058–73]. The alignment was produced using the multisequence alignment program of DNASTAR™ software (DNASTAR Inc, Madison Wis.).

FIG. 3 shows the northern analysis for SEQ ID NO: 2. The northern analysis was produced electronically using LIFESEQ™ database (Incyte Pharmaceuticals, Inc., Palo Alto, Calif.).

DESCRIPTION OF THE INVENTION

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represents the sense or antisense strand. Similarly, "amino acid sequence" as used herein refers to an oligopeptide, peptide, polypeptide, or protein sequence, and fragments or portions thereof, and to naturally occurring or synthetic molecules.

A "composition comprising a given polynucleotide sequence" as used herein refers broadly to any composition containing the given polynucleotide sequence. The composition may comprise an aqueous solution. Compositions comprising polynucleotide sequences encoding IMP (SEQ ID NO: 1) or fragments thereof (e.g., SEQ ID NO: 2 and fragments thereof) may be employed as hybridization probes. In this case, the IMP-encoding polynucleotide sequences are typically employed in an aqueous solution containing salts (e.g., NaCl), detergents (e.g., SDS) and other components (e.g., Denhardt's solution, dry milk, salmon sperm DNA, etc.).

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. "Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

IMP, as used herein, refers to the amino acid sequences of substantially purified IMP obtained from any species, particularly mammalian, including bovine, ovine, porcine, murine, equine, and preferably human, from any source whether natural, synthetic, semi-synthetic, or recombinant. "Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEWTM Fragment Assembly system (GCG, Madison, Wis.), or which has been both extended and assembled.

A "variant" of IMP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic IMP, or any oligopeptide thereof, to induce a specific immune response in appropriate animals or cells and to bind with specific antibodies.

The term "agonist", as used herein, refers to a molecule which, when bound to IMP, causes a change in IMP which modulates the activity of IMP. Agonists may include proteins, nucleic acids, carbohydrates, or any other molecules which bind to IMP.

The terms "antagonist" or "inhibitor", as used herein, refer to a molecule which, when bound to IMP, blocks or modulates the biological or immunological activity of IMP. Antagonists and inhibitors may include proteins, nucleic acids, carbohydrates, or any other molecules which bind to IMP.

The term "modulate", as used herein, refers to a change or an alteration in the biological activity of IMP. Modulation may be an increase or a decrease in protein activity, a change in binding characteristics, or any other change in the biological, functional, or immunological properties of IMP.

The term "mimetic", as used herein, refers to a molecule, the structure of which is developed from knowledge of the structure of IMP or portions thereof and, as such, is able to effect some or all of the actions of stomatin-like molecules.

The term "derivative", as used herein, refers to the chemical modification of a nucleic acid encoding IMP or the encoded IMP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated. "Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A—G—T" binds to the complementary sequence "T—C—A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences. Under "stringent conditions" SEQ ID NO: 2 or fragments thereof will hybridize to its exact complement and closely related sequences. The stringent conditions are chosen such that SEQ ID NO: 2 or fragments thereof will hybridize to sequences encoding human IMP, but not to sequences encoding human stomatin (GI 31068) or the *M tuberculosis* protein (see GI 524225). When fragments of SEQ ID NO: 2 are employed in hybridization reactions, the stringent conditions include the choice of fragments of SEQ ID NO: 2 to be used, unique sequences or regions which are either non-homologous to or which contain less than about 50% homology or complementarity with the nucleotides encoding human stomatin (GI 30168) or the M tuberculosis protein (see GI 1524225).

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO: 1" encompasses the full-length human IMP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding IMP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO: 2 by northern analysis is indicative of the presence of mRNA encoding IMP in a sample and thereby correlates with expression of the transcript from the polynucleotide encoding the protein. "Alterations" in the polynucleotide of SEQ ID NO: 2, as used herein, comprise any alteration in the sequence of polynucleotides encoding IMP including deletions, insertions, and point mutations that may be detected using hybridization assays. Included within this definition is the detection of alterations to the genomic DNA sequence which encodes IMP (e.g., by alterations in the pattern of restriction fragment length polymorphisms capable of hybridizing to SEQ ID NO: 2), the inability of a selected fragment of SEQ ID NO: 2 to hybridize to a sample of genomic DNA (e.g., using allele-specific oligonucleotide probes), and improper or unexpected hybridization, such as hybridization to a locus other than the normal chromosomal locus for the polynucleotide sequence encoding IMP (e.g., using fluorescent in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind IMP polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human integral membrane protein (IMP), the polynucleotides encoding IMP, and the use of these compositions for the diagnosis, prevention, or treatment of diseases associated with abnormal ion transport or membrane conductance. In addition, as mRNA encoding IMP is found in a number of tumors, IMP serves as a marker for cancerous cells, particularly prostate tumor cells.

Nucleic acids encoding the human IMP of the present invention were first identified in Incyte Clone 789094 from the PROSTUT03 cDNA library through a computer-generated search for amino acid sequence alignments. A consensus sequence, SEQ ID NO: 2, was derived from the following overlapping and/or extended nucleic acid sequences: Incyte Clones 220581 (STOMNOT01), 968553 (BRSTNOT05), 748425 (BRAITUT01), 789094 (PROSTUT03), 604240 (BRSTTUT01), 1556986 (BLADTUT04) and 323059 (EOSIHET02).

In one embodiment, the invention encompasses a polypeptide comprising the amino acid sequence of SEQ ID NO: 1, as shown in FIGS. 1A and 1B. IMP is 351 amino acids in length and contains two cysteine residues ($C_{167}$, and $C_{172}$). In addition to providing sites for disulfide bond formation, the cysteine residues provide potential sites for palmitoylation; the stomatin protein, which shares homology with IMP, has been shown to be palmitoylated [Wang, D et al. (1991) J. Biol. Chem. 266:17826]. The human IMP of the present invention contains numerous potential O-linked glycosylation sites (i.e., serine and threonine residues). IMP has two potential N-linked glycoslyation sites (ie., Asn-X-Ser/Thr) (i.e., $N_{96}$ and $N_{154}$). In addition, the human IMP of the present invention contains numerous potential phosphorylation sites (i.e., typically the hydroxyl groups of serine, threonine and tyrosine residues although asparagine, histidine and lysine residues may also be phosphorylated), including potential sites for phosphorylation by cAMP-dependent protein kinase (e.g., R—X—S/T) (ie., $S_{29}$, $T_{36}$, $S_{152}$ and $S_{213}$).

The IMP protein of the present invention, like C. elegans UNC-24, has an acidic isoelectric point (pI). IMP has a pI of 5.91, and UNC-24 has a pI of 5.11.

Figure 2A:
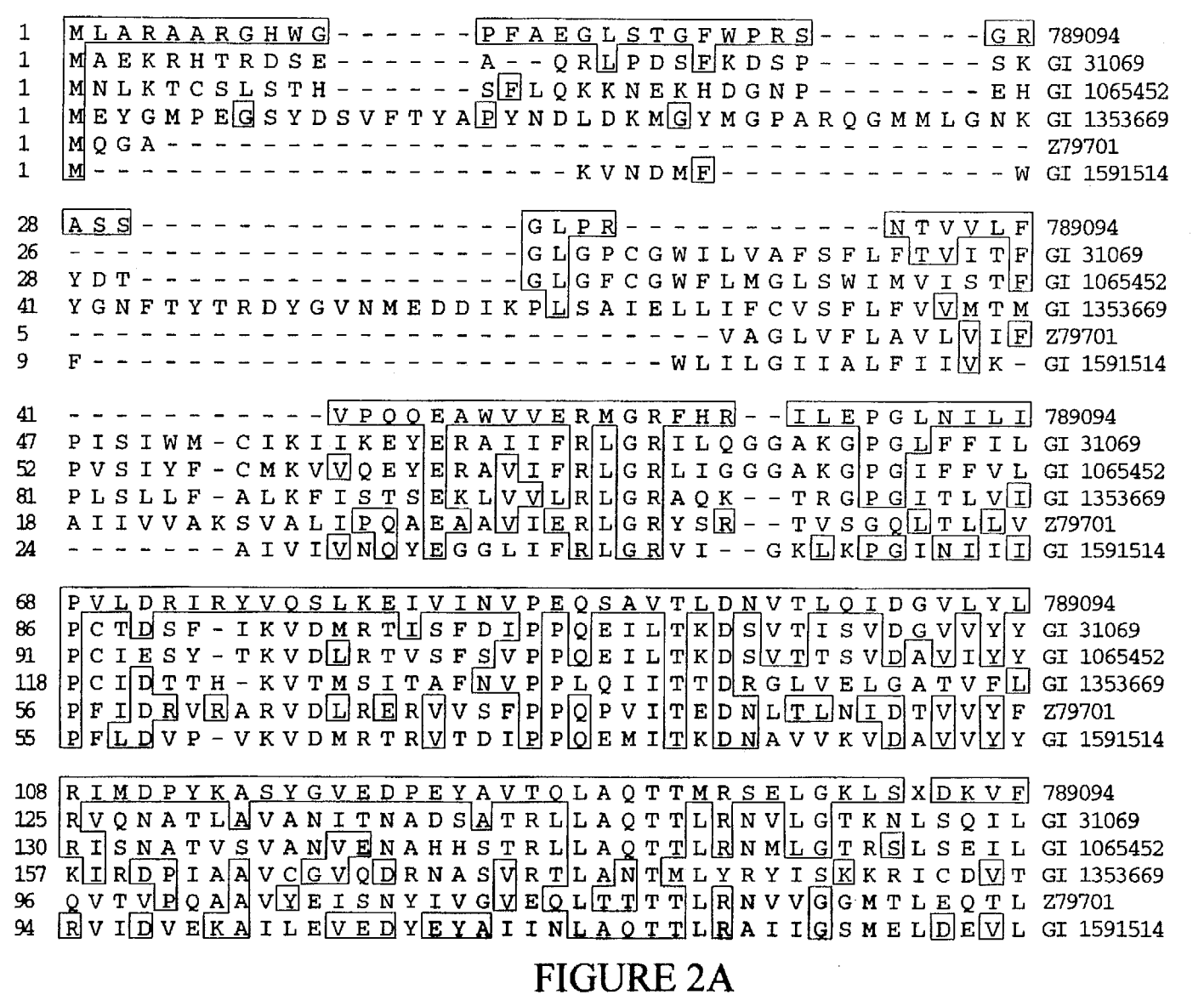
Figure 2B:
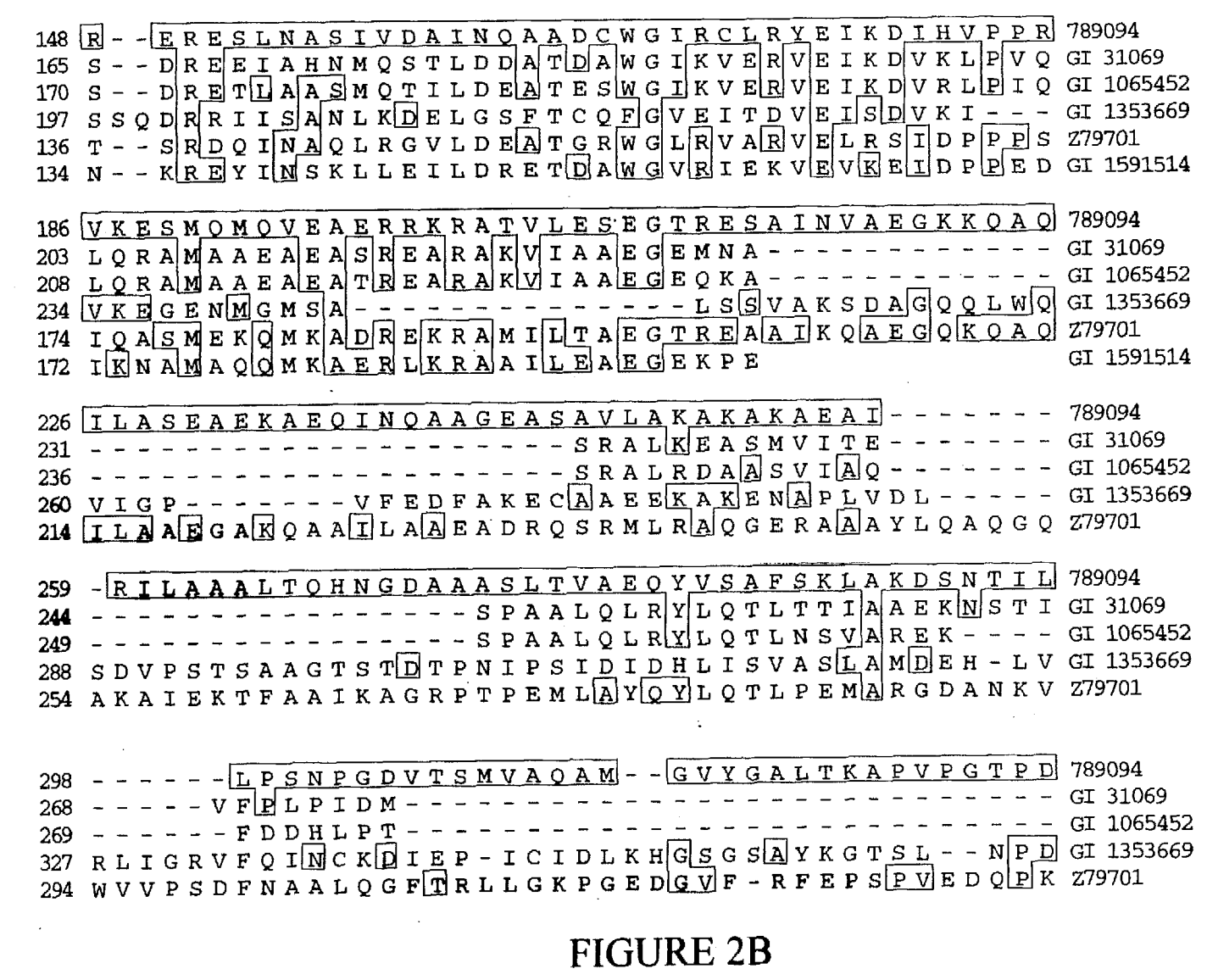

IMP has chemical and structural homology with stomatin (GI 31069; SEQ ID NO: 3), (GI 31069; SEQ ID NO: 3), *C. elegans* MEC-2 protein (GI 1065452; SEQ ID NO: 4), *C. elegans* UNC-24 protein (GI 1353669; SEQ ID NO: 5), a *Mycobacterium tuberculosis* protein of unknown function (Z79701; SEQ ID NO: 6) and a membrane protein from *Methanococcus jannaschii* (GI 1591514; SEQ ID NO: 7). In particular, residues 79-209 of IMP are strongly similar to residues 96-226 of stomatin (33% identity, 60% similarity) and residues 218-253 of IMP are strongly similar to residues 211-246 of stomatin (30% identity, 52% similarity). Residues 79-214 of IMP are strongly similar to residues 101-236 of *C. elegans* MEC-2 (35% identity and 62% similarity). Residues 37-75, 45-71, 83-132, 107-134 and 263-283 of IMP are strongly similar to residues 88-126, 95-121,133-181, 156-183, and 307-326, respectively of *C. elegans* UNC-24 (34% identity and 61% similarity; 41% identity and 63% similarity; 34% identity and 62% similarity; 43% identity and 57% similarity; and 25% identity and 70% similarity, respectively). Residues 38-262 and 187-265 of IMP are strongly similar to residues 26-250 and 186-264, respectively of the M tuberculosis protein (Z79701) (38% identity and 61% similarity; and 36% identity and 63% similarity, respectively). Residues 38-71, 83-211 and 202-222 of IMP are strongly similar to residues 25-58, 69-197 and 177-197, respectively of the *M jannaschii* membrane protein (GI 1591514) (44% identity and 67% similarity; 40% identity and 67% similarity; and 38% identity and 66% similarity, respectively). A pair of residues are said to be similar if they represent conservative substitutions. FIGS. 2A, 2B and 2C provides an alignment between the amino acid sequences of SEQ ID NOs:1 and 3-7.

Northern analysis (FIG. 3) shows the expression of this sequence in various libraries, at least 38% of which are cancerous or immortalized. Of particular note is the expression of IMP mRNA in prostate tumor (2/13), breast tumor (1/13), and pancreatic tumor libraries (1/13). This pattern of expression demonstrates that IMP serves as a marker for cancerous cells, particularly prostate tumor cells.

The invention also encompasses IMP variants. A preferred IMP variant is one having at least 80%, and more preferably 90%, amino acid sequence similarity to the IMP amino acid sequence (SEQ ID NO: 1). A most preferred IMP variant is one having at least 95% amino acid sequence similarity to SEQ ID NO: 1.

The invention also encompasses polynucleotides which encode IMP. Accordingly, any nucleic acid sequence which encodes the amino acid sequence of IMP can be used to generate recombinant molecules which express IMP. In a particular embodiment, the invention encompasses the polynucleotide comprising the nucleic acid sequence of SEQ ID NO: 2 as shown in FIGS. 1A and 1B.

It will be appreciated by those skilled in the art that as a result of the degeneracy of the genetic code, a multitude of nucleotide sequences encoding IMP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring IMP, and all such variations are to be considered as being specifically disclosed.

Although nucleotide sequences which encode IMP and its variants are preferably capable of hybridizing to the nucleotide sequence of the naturally occurring IMP under appropriately selected conditions of stringency, it may be advantageous to produce nucleotide sequences encoding IMP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding IMP and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode IMP and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding IMP or any portion thereof.

Also encompassed by the invention are polynucleotide sequences that are capable of hybridizing to the claimed nucleotide sequences, and in particular, those shown in SEQ ID NO: 2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding IMP which are encompassed by the invention include deletions, insertions, or substitutions of different nucleotides resulting in a polynucleotide that encodes the same or a functionally equivalent IMP. The encoded protein may also contain deletions, insertions, or substitutions of amino acid residues which produce a silent change and result in a functionally equivalent IMP. Deliberate amino acid substitutions may be made on the basis of similarity in polarity, charge, solubility, hydrophobicity, hydrophilicity, and/or the amphipathic nature of the residues as long as the biological activity of IMP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine and; phenylalanine and tyrosine.

Also included within the scope of the present invention are alleles of the genes encoding IMP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (U.S. Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding IMP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055-3060). Additionally, one may use PCR, nested primers, and PromoterFinder™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode IMP, or fusion proteins or functional equivalents thereof, may be used in recombinant DNA molecules to direct expression of IMP in appropriate host cells. Due to the inherent degeneracy of the genetic code, other DNA sequences which encode substantially the same or a functionally equivalent amino acid sequence may be produced and these sequences may be used to clone and express IMP.

As will be understood by those of skill in the art, it may be advantageous to produce IMP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter IMP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding IMP may be ligated to a heterologous sequence to encode a fusion protein. For example, to screen peptide libraries for inhibitors of IMP activity, it may be useful to encode a chimeric IMP protein that can be recognized by a commercially available antibody. A fusion protein may also be engineered to contain a cleavage site located between the IMP encoding sequence and the heterologous protein sequence, so that IMP may be cleaved and purified away from the heterologous moiety.

In another embodiment, sequences encoding IMP may be synthesized, in whole or in part, using chemical methods well known in the art (see Caruthers, M. H. et al. (1980) Nucl.

Acids Res. Symp. Ser. 215-223, Horn, T. et al. (1980) Nucl. Acids Res. Symp. Ser. 225-232). Alternatively, the protein itself may be produced using chemical methods to synthesize the amino acid sequence of IMP, or a portion thereof. For example, peptide synthesis can be performed using various solid-phase techniques (Roberge, J. Y. et al. (1995) Science 269:202-204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) Proteins, Structures and Molecular Principles, W H Freeman and Co., New York, N.Y.). The composition of the synthetic peptides may be confirmed by amino acid analysis or sequencing (e.g., the Edman degradation procedure; Creighton, supra). Additionally, the amino acid sequence of IMP, or any part thereof, may be altered during direct synthesis and/or combined using chemical methods with sequences from other proteins, or any part thereof, to produce a variant polypeptide.

In order to express a biologically active IMP, the nucleotide sequences encoding IMP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding IMP and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding IMP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding IMP, vectors based on SV40 or EBV may be used with an appropriate selectable marker.

In bacterial systems, a number of expression vectors may be selected depending upon the use intended for IMP. For example, when large quantities of IMP are needed for the induction of antibodies, vectors which direct high level expression of fusion proteins that are readily purified may be used. Such vectors include, but are not limited to, the multifunctional E. coli cloning and expression vectors such as Bluescript™ (Stratagene), in which the sequence encoding IMP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding IMP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196.

An insect system may also be used to express IMP. For example, in one such system, Autographa californica nuclear polyhedrosis virus (AcNPV) is used as a vector to express foreign genes in Spodoptera frugiperda cells or in Trichoplusia larvae. The sequences encoding IMP may be cloned into a non-essential region of the virus, such as the polyhedrin gene, and placed under control of the polyhedrin promoter. Successful insertion of IMP will render the polyhedrin gene inactive and produce recombinant virus lacking coat protein. The recombinant viruses may then be used to infect, for example, S. frugiperda cells or Trichoplusia larvae in which IMP may be expressed (Engelhard, E. K. et al. (1994) Proc. Nat. Acad. Sci. 91:3224–3227).

In mammalian host cells, a number of viral-based expression systems may be utilized.

In cases where an adenovirus is used as an expression vector, sequences encoding IMP may be ligated into an adenovirus transcription/translation complex consisting of the late promoter and tripartite leader sequence. Insertion in a non-essential E1 or E3 region of the viral genome may be used to obtain a viable virus which is capable of expressing IMP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding IMP. Such signals include the ATG initiation codon and adjacent sequences. In cases where sequences encoding IMP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express IMP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk or aprt cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsuifiron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, βglucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding IMP is inserted within a marker gene sequence, recombinant cells containing sequences encoding IMP can be identified by the absence of marker gene function. Alternatively, a marker gene can be placed in tandem with a sequence encoding IMP under the control of a single promoter. Expression of the marker gene in response to induction or selection usually indicates expression of the tandem gene as well.

Alternatively, host cells which contain the nucleic acid sequence encoding IMP and express IMP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding IMP can be detected by DNA-DNA or DNA-RNA hybridization or amplification using probes or portions or fragments of polynucleotides encoding IMP. Nucleic acid amplification based assays involve the use of oligonucleotides or oligomers based on the sequences encoding IMP to detect transformants containing DNA or RNA encoding IMP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of IMP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on IMP is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding IMP include oligolabeling, nick translation, end-labeling or PCR amplification using a labeled nucleotide. Alternatively, the sequences encoding IMP, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding IMP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode IMP may be designed to contain signal sequences which direct secretion of IMP through a prokaryotic or eukaryotic cell membrane. When it is desired to express a secreted form of IMP, a polynucleotide sequence encoding a portion of the IMP lacking the hydrophobic stretches located at residues 29–44 and 58–70 of SEQ ID NO: 1 (either or both of these stretches may anchor IMP in the membrane) is preferentially employed.

Other recombinant constructions may be used to join sequences encoding IMP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and IMP may be used to facilitate purification. One such expression vector provides for expression of a fusion protein containing IMP and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying IMP from the fusion protein. A discussion of vectors which contain fusion proteins is provided in Kroll, D. J. et al. (1993; DNA Cell Biol. 12:441–453).

In addition to recombinant production, fragments of IMP may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of IMP may be chemically synthesized separately and combined using chemical methods to produce the full length molecule.

THERAPEUTICS

Based on the chemical and structural homology among IMP (SEQ ID NO: 1) and stomatin (SEQ ID NO: 3), and stomatin-like proteins [e.g., MEC-2 (SEQ ID NO: 4), UNC-24 (SEQ ID NO: 5), the *M tuberculosis* protein (Z79701; SEQ ID NO: 6) and *M jannaschii* membrane protein (GI 1591514; SEQ ID NO: 7), IMP appears to play a role in the regulation of ion channels. Improper functioning of ion channels is associated with a variety of disorders including, but not limited to, hemolytic anemias (e.g., hereditary stomatocytosis, hydrocytosis and xerocytosis). Furthermore, since the sequences encoding IMP were isolated from prostate tumor tissue and IMP is also expressed in breast and pancreatic tumors, IMP expression appears to be indicative of a proliferative cell state.

Therefore, in one embodiment, IMP or a fragment or derivative thereof may be administered to a subject to treat disorders associated with abnormal ion transport or membrane conductance as well as a variety of tumors. Such conditions and diseases may include, but are not limited to, hemolytic anemias and prostate, breast and pancreatic tumors.

In another embodiment, a vector capable of expressing IMP, or a fragment or a derivative thereof, may also be administered to a subject to treat the hemolytic anemias and prostate, breast and pancreatic tumors described above.

In one aspect, agonists of IMP may be used to increase the activity of IMP in cells having reduced IMP-associated ion transport.

In one embodiment, antagonists or inhibitors of IMP may be administered to a subject to treat or prevent tumors, particularly prostate, breast and pancreatic tumors.

In another embodiment, a vector expressing antisense of the polynucleotide encoding IMP may be administered to a subject to treat or prevent tumors, particularly prostate, breast and pancreatic tumors.

In other embodiments, IMP may be administered in combination with other conventional chemotherapeutic agents. The combination of therapeutic agents having different mechanisms of action will have synergystic effects allowing for the use of lower effective doses of each agent and lessening side effects.

Antagonists or inhibitors of IMP may be produced using methods which are generally known in the art. In particular, purified IMP may be used to produce antibodies or to screen libraries of pharmaceutical agents to identify those which specifically bind IMP.

Antibodies which are specific for IMP may be used directly as an antagonist, or indirectly as a targeting or delivery mechanism for bringing a pharmaceutical agent to cells or tissue which express IMP. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which reduce or abolish IMP activity) are especially preferred for therapeutic use.

For the production of antibodies, various hosts including goats, rabbits, rats, mice, humans, and others, may be immunized by injection with IMP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to IMP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of IMP amino acids may be fused with those of another protein such as keyhole limpet hemocyanin and antibody produced against the chimeric molecule.

Monoclonal antibodies to IMP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S.P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce IMP-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for IMP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between IMP and its specific antibody. A two-site, monoclonal-based immunoassay utilizing monoclonal antibodies reactive to two non-interfering IMP epitopes is preferred, but a competitive binding assay may also be employed (Maddox, supra).

In another embodiment of the invention, the polynucleotides encoding IMP, or any fragment thereof, or antisense molecules, may be used for therapeutic purposes. In one aspect, antisense to the polynucleotide encoding IMP may be used in situations in which it would be desirable to block the transcription of the mRNA. In particular, cells may be transformed with sequences complementary to polynucleotides encoding IMP. Thus, antisense molecules may be used to modulate IMP activity, or to achieve regulation of gene finction. Such technology is now well known in the art, and sense or antisense oligomers or larger fragments, can be designed from various locations along the coding or control regions of sequences encoding IMP.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding IMP. These techniques are described both in Sambrook et al. (supra) and in Ausubel et al. (supra).

Genes encoding IMP can be turned off by transforming a cell or tissue with expression vectors which express high levels of a polynucleotide or fragment thereof which encodes IMP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding IMP, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of MRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding IMP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding IMP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of IMP, antibodies to IMP, mimetics, agonists, antagonists, or inhibitors of IMP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of IMP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example IMP or fragments thereof, antibodies of IMP, agonists, antagonists or inhibitors of IMP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind IMP may be used for the diagnosis of conditions or diseases characterized by expression of IMP, or in assays to monitor patients being treated with IMP, agonists, antagonists or inhibitors. The antibodies useful for diagnostic purposes may be prepared in the same manner as those described above for therapeutics. Diagnostic assays for IMP include methods which utilize the antibody and a label to detect IMP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring IMP are known in the art and provide a basis for diagnosing altered or abnormal levels of IMP expression. Normal or standard values for IMP expression are established by combining body fluids or cell extracts taken from normal mammalian subjects, preferably human, with antibody to IMP under conditions suitable for complex formation. The amount of standard complex formation may be quantified by various methods, but preferably by photometric, means. Quantities of IMP expressed in subject, control and disease, samples from biopsied tissues are compared with the standard values. Deviation between standard and subject values establishes the parameters for diagnosing disease.

In another embodiment of the invention, the polynucleotides encoding IMP is used for diagnostic purposes. The polynucleotides which may be used include oligonucleotide sequences, antisense RNA and DNA molecules, and PNAs. The polynucleotides may be used to detect and quantitate gene expression in biopsied tissues in which expression of IMP may be correlated with disease. The diagnostic assay may be used to distinguish between absence, presence, and excess expression of IMP, and to monitor regulation of IMP levels during therapeutic intervention.

In one aspect, hybridization with PCR probes which are capable of detecting polynucleotide sequences, including genomic sequences, encoding IMP or closely related molecules, may be used to identify nucleic acid sequences which encode IMP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding IMP, alleles, or related sequences.

Probes may also be used for the detection of related sequences, and should preferably contain at least 50% of the nucleotides from any of the IMP encoding sequences. The hybridization probes of the subject invention may be DNA or RNA and derived from the nucleotide sequence of SEQ ID NO: 2 or from genomic sequence including promoter, enhancer elements, and introns of the naturally occurring IMP.

Means for producing specific hybridization probes for DNAs encoding IMP include the cloning of nucleic acid sequences encoding IMP or IMP derivatives into vectors for the production of MRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding IMP may be used for the diagnosis of conditions or diseases which are associated with expression of IMP. Examples of such conditions or diseases include cancers of the prostate, pancreas, and breast as well as disorders associated with altered ion conductance. The polynucleotide sequences encoding IMP may be used in Southern or northern analysis, dot blot, or other membrane-based technologies; in PCR technologies; or in dip stick, pin, ELISA or chip assays utilizing fluids or tissues from patient biopsies to detect altered IMP expression. Such qualitative or quantitative methods are well known in the art.

In a particular aspect, the nucleotide sequences encoding IMP provide the basis for assays that detect activation or induction of various cancers, particularly those mentioned above; in addition the lack of expression of IMP may be detected using the IMP-encoding nucleotide sequences disclosed herein. The nucleotide sequences encoding IMP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding IMP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of IMP, a normal or standard profile for expression is established. This may be accomplished by combining body fluids or cell extracts taken from normal subjects, either animal or human, with a sequence, or a fragment thereof, which encodes IMP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding IMP may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of IMP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode IMP may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) Human Chromosomes: A Manual of Basic Techniques, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding IMP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, IMP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between IMP and the agent being tested, may be measured.

Another technique for drug screening which may be used provides for high throughput screening of compounds having suitable binding affinity to the protein of interest as described in published PCT application WO84/03564. In this method, as applied to IMP large numbers of different small test compounds are synthesized on a solid substrate, such as plastic pins or some other surface. The test compounds are reacted with IMP, or fragments thereof, and washed. Bound IMP is then detected by methods well known in the art. Purified IMP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding IMP specifically compete with a test compound for binding IMP. In this manner, the antibodies can be used to detect the presence of any peptide which shares one or more antigenic determinants with IMP.

In additional embodiments, the nucleotide sequences which encode IMP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I PROSTUT03 cDNA Library Construction

The PROSTUT03 cDNA library was constructed from prostate tumor tissue removed from a 76-year-old Caucasian male by radical prostatectomy. The pathology report indicated Mayo grade 3 (of 4) adenocarcinoma (Gleason grade 3+3) in the periphery of the prostate. Perineural invasion was present as was involvement of periprostatic tissue. Non-tumorous portions of the prostate exhibited adenofibromatous hyperplasia. The patient had elevated levels of prostate specific antigen (PSA). Pelvic lymph nodes were negative for tumor. A prior stomach ulcer and atherosclerosis were reported in the patient history; however, the patient was not on any medication at the time of surgery.

The frozen tissue was homogenized and lysed using a Brinkmann Homogenizer Polytron-PT 3000 (Brinkmann Instruments, Inc. Westbury N.Y.) in guanidinium isothiocyanate solution. The lysate was extracted twice with acid phenol at pH 4.0, the first time per Stratagene's RNA isolation protocol (Stratagene Inc, San Diego Calif.). The RNA was precipitated using 0.3 M sodium acetate and 2.5 volumes of ethanol, resuspended in DEPC-treated water, and DNase treated for 25 min at 37° C. The RNA was re-extracted as described above, and MRNA was isolated using the Qiagen Oligotex kit (QIAGEN Inc, Chatsworth Calif.) and used to construct the cDNA library.

The RNA was handled according to the recommended protocols in the SuperScript Plasmid System for cDNA Synthesis and Plasmid Cloning (catalog #18248–013; Gibco/BRL). cDNAs were fractionated on a Sepharose CL4B column (catalog #275105, Pharmacia), and those cDNAs exceeding 400 bp were ligated into pSport I. The plasmid pSport I was subsequently transformed into DH5a™ competent cells (Cat. #18258–012, Gibco/BRL).

II Isolation and Sequencing of cDNA Clones

Plasmid DNA was released from the cells and purified using the Miniprep Kit (Catalog #77468; Advanced Genetic Technologies Corporation, Gaithersburg Md.). This kit consists of a 96-well block with reagents for 960 purifications. The recommended protocol was employed except for the following changes: 1) the 96 wells were each filled with only 1 ml of sterile Terrific Broth (Catalog #22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R rotor at 2900 rpm for 5 minutes was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems, and the reading frame was determined.

III Homology Searching of cDNA Clones and Their Deduced Proteins

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT- 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

A comparison of the full-length and partial cDNA sequences and the deduced amino acid sequences corresponding to the human IMP gene and IMP protein with known nucleotide and protein sequences in GenBank revealed that the full-length human IMP cDNA and protein sequences (i e., SEQ ID NOS: 1 and 2) were unique (i.e., not previously identified). This search revealed that the human IMP protein shared some homology with human stomatin (SEQ ID NO: 3), C. elegans MEC-2 (SEQ ID NO: 4), C. elegans UNC-24 (SEQ ID NO: 5), a protein from *M tuberculosis* (SEQ ID NO: 6) and a membrane protein from *M jannaschii* (SEQ ID NO: 7) (see alignment in FIG. 2A, 2B, and 2C).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the. search is the product score which is defined as:

% sequence identity × % maximum BLAST score/100

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding IMP occurs. Abundance and percent abundance are also reported. Abundance directly reflects the number of times a particular transcript is represented in a cDNA library, and percent abundance is abundance divided by the total number of sequences examined in the cDNA library.

Electronic northern analysis (FIG. 3) revealed that mRNA encoding human IMP (SEQ ID NO: 1) was present in libraries generated from the following tissues: colon, testis, liver, heart, keratinocytes, brain, lung and paraganglia. The expression of IMP in such a wide variety of tissues is similar to the ubiquitous express of stomatin [Stewart, G. W. et al. (1992), supra]. In addition to expression in apparently normal human tissues, IMP was expressed in tumors of the prostate, pancreas and breast as well as in an immortalized cell line.

V Extension of IMP-Encoding Polynucleotides to Full Length or to Recover Regulatory Sequences Full length IMP-encoding nucleic acid sequence (SEQ ID NO: 2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQuick™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2x Carb. The following day, several colonies are randomly picked from each plate and cultured in 150 µl of liquid LB/2x Carb medium placed in an individual well of an appropriate, commercially-available, sterile 96-well microtiter plate. The following day, 5 µl of each overnight culture is transferred into a non-sterile 96-well plate and after dilution 1: 10 with water, 5 µl of each sample is transferred into a PCR array.

For PCR amplification, 18 µl of concentrated PCR reaction mix (3.3x) containing 4 units of rTth DNA polymerase, a vector primer, and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO: 2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 ,µCi of [γ-$^{32}$P] adenosine triphosphate (Amersham) and T4 polynucleotide kinase (DuPont NEN, Boston, Mass.). The labeled oligonucleotides are substantially purified with Sephadex G-25 superfine resin column (Pharmacia & Upjohn). A portion containing 10$^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT ARTM film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the IMP-encoding sequence, or any part thereof, is used to inhibit in vivo or in vitro expression of naturally occurring IMP. Although use of antisense oligonucleotides, comprising about 20 base-pairs, is specifically described, essentially the same procedure is used with larger cDNA fragments. An oligonucleotide based on the coding sequences of IMP, as shown in FIGS. 1A and 1B, is used to inhibit expression of naturally occurring IMP. The complementary oligonucleotide is designed from the most unique 5' sequence as shown in FIGS. 1A and 1B and used either to inhibit transcription by preventing promoter binding to the upstream nontranslated sequence or translation of an IMP-encoding transcript by preventing the ribosome from binding. Using an appropriate portion of the signal and 5' sequence of SEQ ID NO: 2, an effective antisense oligonucleotide includes any 15–20 nucleotides spanning the region which translates into the signal or 5' coding sequence of the polypeptide as shown in FIGS. 1A and 1B.

VIII Expression of IMP

Expression of IMP is accomplished by subcloning the cDNAs into appropriate vectors and transforming the vectors into host cells. In this case, the cloning vector, pSport, previously used for the generation of the cDNA library is used to express IMP in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein or fragments thereof. Sequences encoding IMP fusion proteins lacking the hydrophobic stretches located at residues 29–44 and 58–70 of SEQ ID NO: 1 (either or both of these stretches may anchor IMP in the membrane) are preferentially employed for the production of soluble forms of recombinant IMP. The signal residues present on the pSport vector direct the secretion of IMP into the bacterial growth media which can be used directly in the following assay for activity.

Alternatively, IMP may be expressed as a membrane-bound protein in a host cell and the recombinant IMP recovered from the membrane of the host cell using techniques well known to the art [e.g., Stewart, G. W. (1992), supra].

IX Demonstration of IMP Activity

Given the chemical and structural similarity between IMP and stomatin and stomatin-like proteins (e.g., MEC-2 and UNC-24), IMP is presumed to act as a regulator of an ion channel. To demonstrate IMP's ability to regulate ion channels, cells which normally express IMP [e.g., the HUV—EC—C endothelial cell line (ATCC CRL 1730)] are made deficient in IMP expression (or deficient in IMP activity) and the effect of reduced or absent IMP expression/activity upon the transport of ions is examined. Several methods for the measurement of intracellular ion concentration (e.g., $Na^+$ and $K^+$) and the measurement of ion flux are known to the art [see, e.g., Stewart, G. W. et al. (1992), supra, Stewart, G. W. (1988) J. Physiol. (Lond) 401:1, and Stein, W. D. (1990) Channels, Carriers and Pumps, Acad. Press, London].

The expression of IMP may be reduced or abolished by introduction of a sufficient amount of antisense IMP molecules. Antisense transcripts may be introduced by transformation of the IMP-expressing cell with an expression vector which produced antisense IMP transcripts or alternatively, antisense IMP transcripts may be chemically synthesized and introduced (e.g., via microinjection, electroporation, liposome fusion) into the IMP-expressing cell. The activity of IMP in an IMP-expressing cell may be reduced or abolished by the introduction of anti-IMP antibodies capable of neutralizing the activity of IMP.

Following the introduction of either anti-IMP antibodies or antisense IMP transcripts to generate modified cells, the ability of the cell to maintain proper ion conductance is examined using standard techniques. Failure of the modified cells to maintain proper ion conductance indicates that IMP regulates an ion channel. This is further demonstrated by restoration of proper ion conductance by the addition of purified IMP (prepared as described in Ex. VIII) to the modified cells (purified IMP may be introduced into the modified cells by a variety of means including direct injection, electroporation, liposome fusion, etc.).

X Production of IMP Specific Antibodies

IMP that is substantially purified using PAGE electrophoresis (Sambrook, supra), or other purification techniques, is used to immunize rabbits and to produce antibodies using standard protocols. The amino acid sequence deduced from SEQ ID NO: 2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 43 1A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring IMP Using Specific Antibodies

Naturally occurring or recombinant IMP is substantially purified by immunoaffinity chromatography using antibodies specific for IMP. An immunoaffinity column is constructed by covalently coupling IMP antibody to an activated chromatographic resin, such as CnBr-activated Sepharose (Pharmacia & Upjohn). After the coupling, the resin is blocked and washed according to the manufacturer's instructions.

Media containing IMP is passed over the immunoaffinity column, and the column is washed under conditions that allow the preferential absorbance of IMP (e.g., high ionic strength buffers in the presence of detergent). The column is eluted under conditions that disrupt antibody/IMP binding (eg, a buffer of pH 2–3 or a high concentration of a chaotrope, such as urea or thiocyanate ion), and IMP is collected.

XII Identification of Molecules Which Interact with IMP

IMP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled IMP, washed and any wells with labeled IMP complex are assayed. Data obtained using different concentrations of IMP are used to calculate values for the number, affinity, and association of IMP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A composition comprising isolated and purified polynucleotide sequence encoding the integral membrane protein having the amino acid sequence represented by SEQ. ID NO: 1.

2. A polynucleotide sequence which hybridizes under stringent conditions to the polynucleotide sequence of claim 1.

3. An isolated and purified polynucleotide sequence represented by SEQ ID NO: 2.

4. A polynucleotide sequence which is complementary to SEQ ID NO: 2.

5. A composition comprising the polynucleotide sequence of claim 4.

6. An expression vector containing the polynucleotide sequence of claim 1.

7. A host cell containing the vector of claim 6.

8. A method for producing a polypeptide represented by the amino acid sequence of SEQ ID NO: 1, the method comprising the steps of:
    a) culturing the host cell of claim 7 under conditions suitable for the expression of the polypeptide; and
    b) recovering the polypeptide from the host cell culture.

\* \* \* \* \*